(12) United States Patent
Marine et al.

(10) Patent No.: US 9,783,803 B2
(45) Date of Patent: Oct. 10, 2017

(54) INHIBITION OF NEAT1 FOR TREATMENT OF SOLID TUMORS

(71) Applicants: VIB VZW, Ghent (BE); Katholieke Universiteit Leuven, K.U. Leuven R&D, Leuven (BE)

(72) Inventors: Jean-Christophe Marine, Brussels (BE); Laura Standaert, Zottegem (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 15/116,184

(22) PCT Filed: Feb. 9, 2015

(86) PCT No.: PCT/EP2015/052663
§ 371 (c)(1),
(2) Date: Aug. 2, 2016

(87) PCT Pub. No.: WO2015/118156
PCT Pub. Date: Aug. 13, 2015

(65) Prior Publication Data
US 2017/0009229 A1    Jan. 12, 2017

(30) Foreign Application Priority Data
Feb. 7, 2014   (EP) .................................. 14154284

(51) Int. Cl.
| | | |
|---|---|---|
| C12N 15/113 | (2010.01) | |
| C07H 21/02 | (2006.01) | |
| C07H 21/04 | (2006.01) | |
| A61K 31/7088 | (2006.01) | |
| A61K 31/713 | (2006.01) | |
| A61K 45/06 | (2006.01) | |

(52) U.S. Cl.
CPC ........ *C12N 15/113* (2013.01); *A61K 31/7088* (2013.01); *A61K 31/713* (2013.01); *A61K 45/06* (2013.01); *C12N 2310/113* (2013.01); *C12N 2310/14* (2013.01); *C12N 2310/3231* (2013.01); *C12N 2310/341* (2013.01); *C12N 2320/31* (2013.01)

(58) Field of Classification Search
None
See application file for complete search history.

(56) References Cited

U.S. PATENT DOCUMENTS

| | | |
|---|---|---|
| 2007/0179160 A1 | 8/2007 | Helleday |
| 2013/0225659 A1 | 8/2013 | Bennett |
| 2013/0237585 A1 | 9/2013 | Bennett et al. |
| 2014/0371296 A1 | 12/2014 | Bennett |
| 2015/0005327 A1 | 1/2015 | Helleday |

FOREIGN PATENT DOCUMENTS

| | | |
|---|---|---|
| WO | 2005012524 | 2/2005 |
| WO | 2012012443 | 1/2012 |
| WO | 2012012467 | 1/2012 |
| WO | 2013096837 | 6/2013 |
| WO | 2014031881 | 2/2014 |
| WO | 2015118156 | 8/2015 |

OTHER PUBLICATIONS

Kim et al (BMC Cancer 2010, 10:576).*
Pils et al (BMC Cancer 2013, 13:178).*
Ishiyama et al (Cancer Sci98(1): 50-57, 2007).*
You et al (Indian J. Cancer (51:e77-e81, Special Issue Feb. 2014).*
Maeda et al (Oncology Reports 31: 551-556, 2014).*
Zhang et al., NEAT1 Long Noncoding RNA and Paraspeckle Bodies Modulate HIV-1 Posttranscriptional Expression, mBio, Jan. 2013, pp. 1-9, vol. 4, Issue 1.
Nishimoto et al., The long non-coding RNA nuclear-enriched abundant transcript 1_2 induces paraspeckle formation in the motor neuron during the early phase of amyotrophic lateral sclerosis, Molecular Brain, 2013, pp. 1-18, vol. 6, Issue 31.
Clemson et al., An Architectural Role for a Nuclear Non-coding RNA: NEAT1 RNA is Essential for the Structure of Paraspeckles, Mol Cell., Mar. 27, 2009, pp. 717-726, vol. 33, Issue 6.
Tao et al., miR-612 suppresses the invasive-metastatic cascade in hepatocellular carcinoma, Journal of Experimental Medicine, 2013, pp. 789-803, vol. 210, No. 4.
PCT International Search Report, PCT/EP2015/052663 dated Apr. 24, 2015.
PCT International Written Opinion, PCT/EP2015/052663 dated Apr. 24, 2015.

* cited by examiner

*Primary Examiner* — Richard Schnizer
(74) *Attorney, Agent, or Firm* — TraskBritt P.C.

(57) ABSTRACT

The application relates to the field of cancer, particularly to the field of solid tumors. It was found that a particular long non-coding RNA (lncRNA), NEAT1, an essential architectural component of nuclear paraspeckles, is required for the survival of cancer, but not that of normal, non-transformed, cells. Inhibition of NEAT1 reduces cell viability of cancer cells and induces apoptosis. These data identify NEAT1 as a novel therapeutic target for treatment of solid tumors.

13 Claims, 13 Drawing Sheets
(10 of 13 Drawing Sheet(s) Filed in Color)

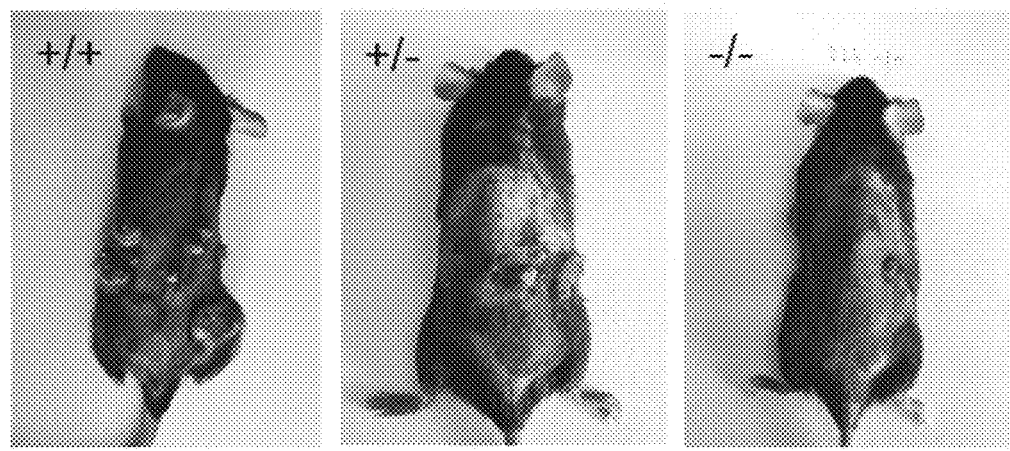
*FIG. 6C*
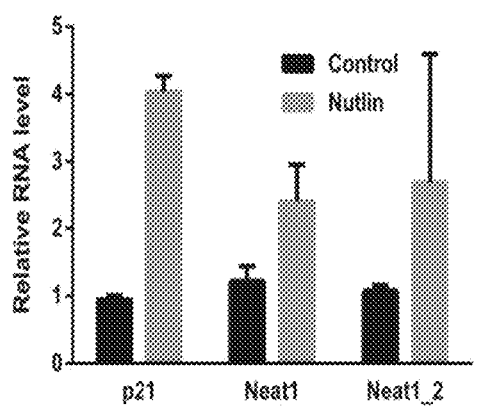
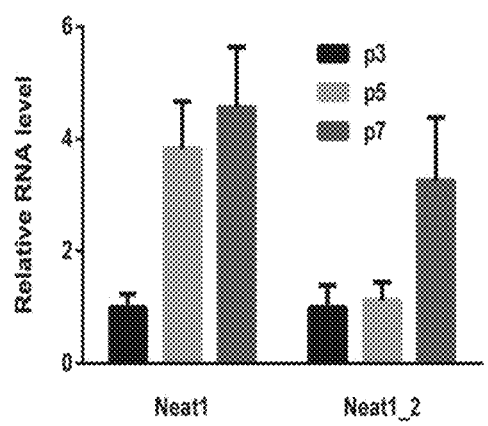
*FIG. 7A*  *FIG. 7B*

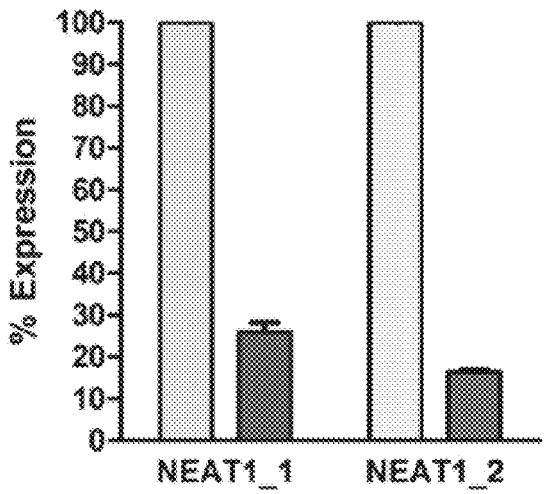
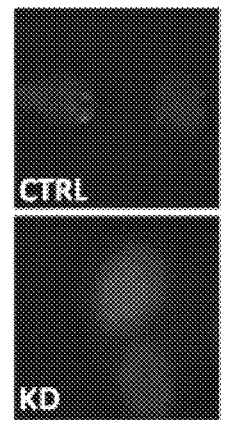
FIG. 8A    FIG. 8B
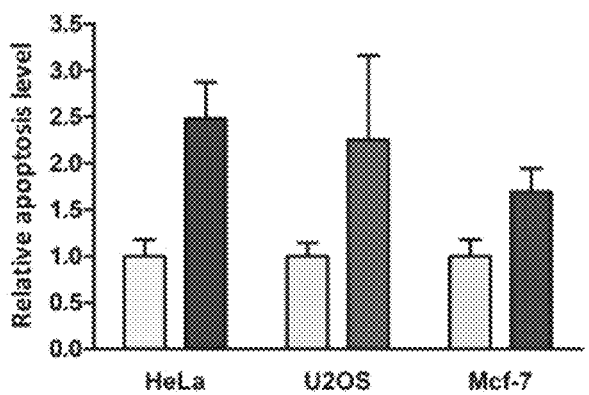
FIG. 8C
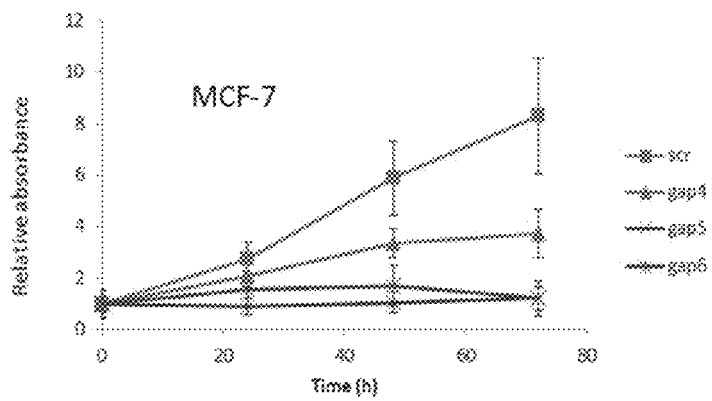
FIG. 8D

INHIBITION OF NEAT1 FOR TREATMENT OF SOLID TUMORS

CROSS-REFERENCE TO RELATED APPLICATIONS

This application is a national phase entry under 35 U.S.C. §371 of International Patent Application PCT/EP2015/052663, filed Feb. 9, 2015, designating the United States of America and published in English as International Patent Publication WO 2015/118156 A1 on Aug. 13, 2015, which claims the benefit under Article 8 of the Patent Cooperation Treaty to European Patent Application Serial No. 14154284.5, filed Feb. 7, 2014.

TECHNICAL FIELD

The present application relates to the field of cancer, particularly to the field of solid tumors. It was found that a particular long non-coding RNA (lncRNA), NEAT1, an essential architectural component of nuclear paraspeckles, is required for the survival of cancer, but not that of normal, non-transformed cells. Inhibition of NEAT1 reduces cell viability of cancer cells and induces apoptosis. These data identify NEAT1 as a novel therapeutic target for treatment of solid tumors.

BACKGROUND p53 is the archetypal tumor suppressor, but still a lot remains to be learned about the mechanisms by which p53 exerts its tumor suppressor function. Many target genes have been described, both direct and indirect targets, transcription factors, both protein coding genes and non-coding genes (e.g., miRNAs). However, although it is generally accepted that p53 is a master apoptosis regulator, it is still unknown how p53 makes the switch from arrest/survival to apoptosis. As p53 in some cases even seems to help tumorigenesis, it would be advantageous to identify mechanisms by which p53 stimulates or prevents apoptosis, particularly of cancer cells.

Moreover, since cancer cells have developed an increased ability to survive in sub-optimal environment, even irrespective of the presence or absence of wild-type p53, it would be advantageous to identify targets that can modulate cell survival downstream of p53. Most preferably, such targets would allow selective modulation of the pathway in cancer cells, so that these cells can be selectively killed.

BRIEF SUMMARY

Using RNAseq and ChIPseq experiments, NEAT1 was identified as a direct target gene of p53. NEAT1 is an abundant nuclear long non-coding RNA that functions as an essential architectural component of nuclear paraspeckles. Although the function of paraspeckles remains unclear, transfection studies indicate that they modulate gene transcription and/or mRNA translation through sequestration of specific transcription factors and/or edited mRNAs, respectively.

To investigate the physiological role of paraspeckles in vivo, mice that lack NEAT1 were generated. NEAT1 knock-out (KO) mice are viable and have no apparent phenotype except for a defect in pubertal mammary gland branching morphogenesis along with reduced lobular-alveolar development during pregnancy and lactation capacity.

Despite the previous observation that NEAT1 expression and paraspeckles formation increases upon passages, it is shown herein that NEAT1-deficient Mouse Embryonic Fibroblasts (MEFs) do not exhibit any significant growth defects indicating that NEAT1 and paraspeckles are dispensable for the proliferation and survival of normal, non-transformed cells. In contrast, cultured cancer cells are dependent on NEAT1 expression for their survival. Knocking-down NEAT1 using LNA-modified antisense oligonucleotides drastically decreases the number of paraspeckles, the metabolic activity and viability of a wide variety of cancer cell lines.

Although the lncRNA NEAT1 plays critical roles in vivo during mammary gland morphogenesis, its expression is, by and large, dispensable during adulthood. Together with the observation that NEAT1 is required for the survival of cancer, but not normal/non-transformed cells, these data identify NEAT1 as a therapeutic target for cancer therapy.

Provided are inhibitors of functional expression of the NEAT1 gene. Such inhibitors can act at the DNA level or at the RNA (i.e., gene product) level. As NEAT1 is a non-coding gene, there is no protein product for this gene.

According to a further aspect, the inhibitors of functional expression of NEAT1 are provided for use as a medicament. According to yet further aspects, the inhibitors of functional expression of NEAT1 are provided for use in treatment of cancer, in particular, for use in treatment of solid tumors. In still further embodiments, the inhibitors are provided for use in treatment of carcinoma (i.e., cancers derived from epithelial cells). According to alternative embodiments, the inhibitors are provided for use in treatment of cancers selected from the group of breast cancer, skin cancer, osteosarcoma, colorectal cancer, and neuroblastoma. According to very specific embodiments, the skin cancer is non-melanoma skin cancer, typically selected from BCC (basal cell carcinoma) or SCC (squamous cell carcinoma).

This is equivalent to saying that methods of treating a solid tumor in a subject in need thereof are provided, the method comprising administering an inhibitor of functional expression of NEAT1 to the subject. Likewise, it is equivalent to providing methods of treating carcinoma, or methods of treating a cancer selected from the group of breast cancer, skin cancer, osteosarcoma, colorectal cancer, and neuroblastoma, wherein an inhibitor of functional expression of NEAT1 is provided to the subject.

The nature of the inhibitor is not vital to the disclosure, as long as it inhibits the functional expression of the NEAT1 gene. According to specific embodiments, the inhibitor is selected from a gapmer, an shRNA, an siRNA, a CRISPR, a TALEN, a Zinc-finger nuclease or a small molecule. According to specific embodiments, the inhibitor is administered to, or is targeted to, cancer cells (such as solid tumor cells).

According to alternative, but not exclusive, specific embodiments, the inhibitor selectively induces apoptosis in cancer cells. This particularly implies that it induces apoptosis in cancer (e.g., carcinoma) cells, but not in normal (non-transformed) similar cells (e.g., epithelial cells). According to further specific embodiments, the inhibitor induces apoptosis independent of p53 status, e.g., independent whether p53 has particular mutations or not, or independent of its expression levels.

It is shown herein that NEAT1 inhibition interferes with DNA repair pathways, particularly with the double-strand repair mechanisms such as homologous recombination (HR) and non-homologous end joining (NHEJ). This means that cells in which NEAT1 is inhibited will be particularly sensitive to inhibition of the remaining single-strand repair pathways (excision repair pathways), such as base excision repair (BER), whereas cells in which NEAT1 is not inhibited will be a lot less sensitive to this treatment.

Thus, according to particular embodiments, combinations of an inhibitor of a DNA excision repair enzyme with an inhibitor of functional expression of NEAT1 are provided for use in the treatment of cancer. This is envisaged to induce synthetic lethality in cells.

According to specific embodiments, the inhibitor of a DNA excision repair enzyme is an inhibitor of a DNA base excision repair enzyme. According to further specific embodiments, the inhibitor of a DNA base excision repair enzyme is a PARP inhibitor.

Furthermore, it is shown herein that NEAT1 controls mitochondria dynamics and that this could also contribute to its oncogenic activities. NEAT1 is required for expression of MFF, which, in turn, modulate mitochondria fission. Loss of NEAT1 leads to a robust decrease in MFF expression and eventually to swollen mitochondria and increased sensitivity to oxidative stress and/or oncogenic stress. Targeting NEAT1 makes the cancer cells extremely sensitive to oxidative stress. Thus, according to particular embodiments, combinations of an agent that increases oxidative stress with an inhibitor of functional expression of NEAT1 are provided for use in the treatment of cancer. This is also envisaged to induce synthetic lethality in cells. Examples of such agents that increase oxidative stress are known in the art and include (but are not limited to), e.g., rotenone, $H_2O_2$, tBHP, and okadaic acid.

According to a similar aspect, methods of treating cancer are provided, comprising administering an inhibitor of functional expression of NEAT1 to a subject in need thereof, which methods may further entail administering an inhibitor of a DNA base excision repair enzyme. This can be done as a combination treatment (i.e., concomitant or simultaneous administration) or can be done by separate administration of the compounds, but particularly by subsequent administration (i.e., within a limited time frame of each other, so that both inhibitors are simultaneously active in the subject).

According to a further aspect, methods are provided that may identify whether a tumor is suitable for treatment with an inhibitor of functional expression of NEAT1. These methods typically have the following steps:
  Determining whether expression of NEAT1 is increased in the tumor or a sample of tumor cells; and
  Establishing whether the tumor is suitable for treatment, wherein increased expression is indicative of suitability for treatment.

Typically, the tumor will be a solid tumor. Thus, the methods may entail a first step of providing a sample of (solid) tumor cells. The determining step may occur purely in vitro, i.e., without a step interacting on the human or animal body.

According to particular embodiments, the tumor is a carcinoma. According to alternative embodiments, the tumor is selected from breast cancer, skin cancer, osteosarcoma, colorectal cancer, and neuroblastoma.

According to specific embodiments, when it is established that the tumor is suitable for treatment, the methods may further comprise a step of administering an inhibitor of functional expression of NEAT1 to the subject in which the tumor is present. This is in order to treat the tumor.

These inhibitors may be further combined with, e.g., an inhibitor of a DNA excision repair enzyme, or an agent that increases oxidative stress.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A: MCF-7 cells were exposed to Nutlin3a (for 24 hours) and paraspeckles formation (red dots) was assessed by FISH-analysis with a NEAT1-specific probe set. Nuclei were counter-stained with DAPI (Blue). FIG. 3B: Quantification of paraspeckles formation in MCF-7 cells exposed to Nutlin3a before (mock) and after transfection of the cells with a control/scramble gapmer (scr) or gapmers targeting the NEAT1 transcripts (gap4 and gap6).

FIG. 4A), low doses of Rotenone (Rot; FIG. 4B) that promotes oxidative stress, low doses of doxorubicin (Doxo, FIG. 4C) and replicative stress-induced damage (RS; FIG. 4D). NEAT1 is not significantly induced in cells exposed to apoptotic-inducing stress level such as high doses of Doxo (FIG. 4E) and high doses of irradiation (12 Gy; FIG. 4F).

FIGS. 6A-6C. Tumor development is significantly altered in NEAT1 KO (−/−) mice exposed to a two-stage chemically induced carcinogenesis protocol. (FIG. 6A) Number of papillomas per mouse (n=31) after 8 months of DMBA/TPA treatment; significance determined by unpaired two-tailed t-test. (FIG. 6B) Percentage of mice with squamous cell carcinomas in the same experiment (n=31, p-value 0.0072, chi-square test). (FIG. 6C) Representative pictures of the mice are shown.

FIGS. 7A-7F. NEAT1 is required for primary cells immortalization. NEAT1 expression in induced in mouse embryonic fibroblasts (MEFs) upon Nutlin3a exposure (FIG. 7A) and replicative passaging on a 3T3 protocol (FIG. 7B). Although the growth of NEAT1 KO MEFs is comparable to wild-type controls at early passages (FIG. 7C), NEAT1 KO cells enter apoptosis and cannot be immortalized at late passages (FIGS. 7D-7F) in contrast to the WT MEFs. Since immortalization of MEFs is invariably associated with inactivation of the p53 pathway, this result indicates that NEAT1 and p53 may be synthetically lethal.

FIGS. 8A-8D. NEAT1 KD reduces the cell viability of human cancer cell lines. Gapmers 4 and 5 (gap 4 and 5) were used to knock-down the expression of all NEAT1 isoforms, and Gapmer 6 (gap 6) to specifically KD expression of the long isoform, in a series of cancer cell lines. Transfection of gaps 4 and 5 causes a robust decrease in NEAT1 expression (FIG. 8A) and paraspeckles formation (FIG. 8B), and induction of apoptosis as measured using a caspase 3/7 glow assay (FIG. 8C) and by FACS analysis. Transfection of gap 4, gap 5 and gap 6 all decrease MCF-7 growth significantly as measured using a WST1-assay (FIG. 8D).

(FIG. 9C) Top panel shows efficient KD of the different NEAT1 isoforms with the gapmers, as shown by relative RNA levels. SCR: scrambled control. Blue bars, all NEAT1 isoforms. Green bars, long NEAT1 isoform. Low panel shows NEAT1 KD cells accumulate more damage than control cells upon exposure of U2OS cells to low concentrations of the DNA-damaging agent bleomycin. This result is consistent with a reduced ability of NEAT1 KD cells to repair DNA damage.

(FIG. 10A) This panel shows efficient KD of the different NEAT1 isoforms with the gapmers, as shown by relative RNA levels 24 hours and 48 hours post-transfection. N1C: scrambled control (red bars); N1KD NEAT1_1 and NEAT1_2 KD (orange bars). (FIG. 10B) MFF mRNA relative expression in various cancer cell lines upon NEAT1 KD. This figure shows that MFF transcription is highly dependent upon NEAT1 expression.

(FIG. 11A) Western blotting showing that the p53 functionality is exacerbated in NEAT1 KD cells following exposure to Nutlin3a (in MCF7 cells) and consequently Nutlin3a-induced apoptosis is increased (as exemplified by an increase in PARP cleavage) upon NEAT1 KD. (FIG. 11B) mRNA expression levels of the p53-canonical target gene, p21, is increased in NEAT1 KD cells, in particular, upon exposure to Nutlin3a; this data confirm an increase in p53 transcriptional activity in these experimental conditions.

DETAILED DESCRIPTION

Definitions

Figure 1:
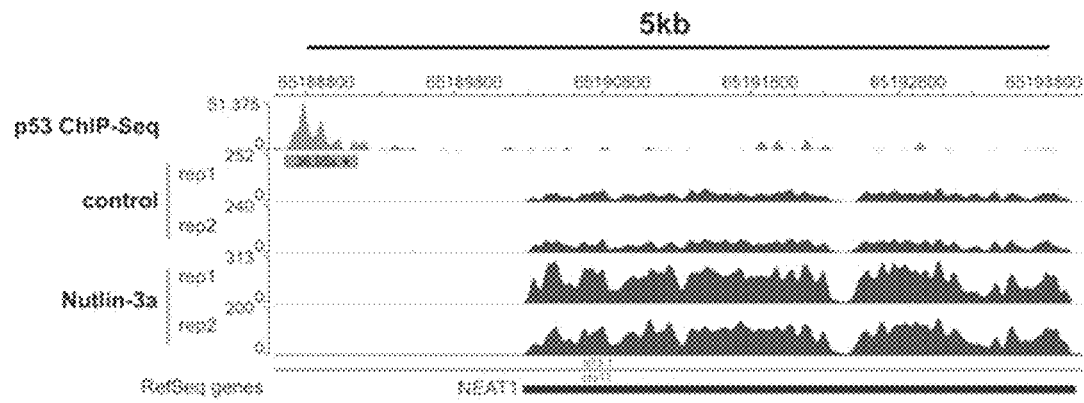
FIG. 1 provides evidence that NEAT1 is a direct p53 target gene in the breast cancer cell line MCF-7. RNA-seq and p53 ChIPseq experiments have been carried out in MCF-7 cells following exposure to the MDM2 antagonist Nutlin3a for 24 hours. The NEAT1 locus is shown and the RNA-seq peaks in blue are shown in untreated (Control) cells and in Nutlin3a-treated cells for 24 hours (two biological replicates are shown), the increase in intensity of the peaks from 0 (control) to 24 hours indicate that Nutlin3a induces transcription of NEAT1. The p53-ChIP peaks are shown in green; these peaks indicate that p53 is directly recruited to the NEAT1 promoter upon Nutlin3a exposure.

This disclosure will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments described herein are capable of operation in other sequences than described or illustrated herein.

The following terms or definitions are provided solely to aid in the understanding of the disclosure. Unless specifically defined herein, all terms used herein have the same meaning as they would to one skilled in the art. Practitioners are particularly directed to Sambrook et al., *Molecular Cloning: A Laboratory Manual*, $2^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

The term "NEAT1" as used herein refers to the gene nuclear paraspeckle assembly transcript 1 (sometimes also referred to as nuclear enriched abundant transcript 1, and previously sometimes known as TncRNA), Gene ID: 283131 in humans, as well as the mRNA that is transcribed from the gene. As it is a non-protein coding gene, there is no protein product. The human gene has different transcripts (or splice variants), the nomenclature of which is not entirely consistent. As used herein, NEAT1_1 refers to Genbank accession number NR 028272 (with a transcript length of 3756 bp), the term NEAT1_2 is used for the longest transcript of over 20 kb (22743 bp for GenBank accession HG503867; transcript ID ENST00000501122 in Ensembl (but there referred to as NEAT1_1) or 21760 bp for UCSC link uc010rog.2). Other reported transcripts include, e.g., GenBank accession HG503866 (transcript ID ENST00000499732 in Ensembl (but there referred to as NEAT1_2) with a length of 1745 bp), accession no. EF177379 (3729 bp), NEAT1_202 (transcript ID ENST00000601801, 1457 bp) and NEAT1_201 (transcript ID ENST00000384994, 100 bp miRNA).

Both the NEAT1_1 and NEAT1_2 transcripts are lincRNA (large intergenic non-coding RNAs).

Unless specifically mentioned otherwise, the term NEAT1 encompasses the different isoforms. Fragments of NEAT1 are also envisaged, as long as they are functionally active (for instance, if they are able to form paraspeckles). According to particular embodiments, the NEAT1 gene product refers to the long transcript(s), particularly the >20 kb transcripts, that are a structural part of paraspeckles (i.e., particularly NEAT1_2).

With "functional expression" of NEAT1 is meant the transcription and/or translation of functional gene product. For non-protein coding genes like NEAT1, "functional expression" can be deregulated on at least two levels. First, at the DNA level, e.g., by absence or disruption of the gene, or lack of transcription taking place (in both instances, preventing synthesis of the relevant gene product). The lack of transcription can, e.g., be caused by epigenetic changes (e.g., DNA methylation) or by loss of function mutations. A "loss-of-function" or "LOF" mutation as used herein is a mutation that prevents, reduces or abolishes the function of a gene product as opposed to a gain-of-function mutation that confers enhanced or new activity on a protein. LOF can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product. Also included within this definition are mutations in promoters or regulatory regions of the NEAT1 gene if these interfere with gene function. A null mutation is an LOF mutation that completely abolishes the function of the gene product. A null mutation in one allele will typically reduce expression levels by 50%, but may have severe effects on the function of the gene product. Note that functional expression can also be deregulated because of a gain of function mutation: by conferring a new activity on the protein, the normal function of the protein is deregulated, and less functionally active protein is expressed.

Second, at the RNA level, e.g., by lack of efficient translation taking place, for example, because of destabilization of the mRNA (e.g., by UTR variants) so that it is degraded before translation occurs from the transcript, or by lack of efficient transcription, e.g., because a mutation introduces a new splicing variant.

The term "status" as used in the application with regard to a particular protein, specifically tumor-associated proteins (e.g., p53 status, Myc status), refers to the mutational status and/or the expression of these particular proteins. Typically, the term is used in the sense "irrespective of" or "independent of" status, meaning that an effect is observed irrespective of expression levels of, or presence of mutations in, the particular protein (e.g., p53, Myc status).

"Long non-coding RNAs" (long ncRNAs, lncRNA) as used herein are non-protein coding transcripts longer than 200 nucleotides. A particular class of lncRNA are long intergenic ncRNAs (lincRNA), referring to long non-coding RNAs that are transcribed from non-coding DNA sequences between protein-coding genes.

A "solid tumor" or "neoplasm" as used herein refers to an abnormal mass of tissue as a result of abnormal growth or division of cells. Typically, these tumors are malignant. The term does not encompass blood tumors (leukemia, lymphoma, multiple myeloma). These tumors are typically characterized by epigenetic abnormalities (chromosomal translocations) that are uncommon in solid tumors.

"Carcinoma" as used herein refers to cancers derived from epithelial cells.

An "inhibitor of a DNA base excision repair enzyme" as used herein refers to a substance that can interfere with the base excision repair function of the gene product, either at the DNA level (by inhibiting the formation of the relevant gene product, i.e., by preventing or interfering with transcription), at the RNA level (by neutralizing or destabilizing mRNA to prevent or interfere with translation) or at the protein level (by neutralizing or inhibiting the protein involved in BER). It is particularly envisaged that the inhibitor is a PARP inhibitor, as such inhibitors are well characterized. Most particularly envisaged are inhibitors of PARP-1 and/or of PARP-2, as these enzymes are the PARPs most actively involved in BER. However, inhibitors of other PARPs may be useful as well. In this regard, recent publications suggest that the PARP inhibitor iniparib, which is explicitly envisaged for use, inhibits PARPs other than PARP-1 and 2, particularly PARP-5 and 6 (J. Ji, M. P. Lee, M. Kadota, et al., Pharmacodynamic and pathway analysis of three presumed inhibitors of poly (ADP-ribose) polymerase: ABT-888, AZD 2281, and BSI201, *Proceedings of the* 102*nd Annual Meeting of the American Association for Cancer Research* 2011 Apr. 2-6, Orlando, Fla. AACR. 2011, Abstract nr 4527; K. A. Maegley, P. Bingham, J. H. Tatlock, et al., All PARP inhibitors are not equal: an in vitro mechanistic comparison of PF-01367338 to iniparib, *J. Clin. Oncol.* 2011, 29 (suppl; abstr e13576); R. A. Nagourney, K. R. Kenyon, F. R. Francisco, et al., Functional analysis of PARP inhibitors AZD 2281 and BSI-201 in human tumor primary cultures: a comparison of activity and examination of synergy with cytotoxic drugs, *J. Clin. Oncol.* 2011, 29 (suppl; abstr e13599)).

The present application is the first to show that NEAT1 expression can be dispensed with in normal, non-transformed cells, while its expression is important for the survival of cancer cells. Consequently, inhibition of NEAT1 lncRNA can be used to selectively induce apoptosis in cancer cells, particularly solid tumor cells, most particularly carcinoma cells.

Accordingly, provided are inhibitors of functional expression of the NEAT1 gene. Such inhibitors can act at the DNA level, or at the RNA (i.e., gene product) level. As NEAT1 is a non-coding gene, there is no protein product for this gene.

If inhibition is to be achieved at the DNA level, this may be done using gene therapy to knock-out or disrupt the target gene. As used herein, a "knock-out" can be a gene knockdown or the gene can be knocked out by a mutation such as a point mutation, an insertion, a deletion, a frameshift, or a missense mutation by techniques known in the art including, but not limited to, retroviral gene transfer. Another way in which genes can be knocked out is by the use of zinc finger nucleases. Zinc-finger nucleases (ZFNs) are artificial restriction enzymes generated by fusing a zinc finger DNA-binding domain to a DNA-cleavage domain. Zinc finger domains can be engineered to target desired DNA sequences that enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double-strand breaks (DSB). The DNA binding domain of a TALEN® is capable of targeting with high precision a large recognition site (for instance, 17 bp). Meganucleases are sequence-specific endonucleases, naturally occurring "DNA scissors," originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes).

Another recent genome editing technology is the CRISPR/Cas system, which can be used to achieve RNA-guided genome engineering. CRISPR is an acronym for Clustered Regularly Interspaced Short Palindromic Repeats, i.e., DNA loci that contain multiple, short, direct repetitions of base sequences. "Cas" stands for CRISPR ASsociated genes. Plasmids with cas genes and specifically designed CRISPR regions can be used to modify a host genome at any location (Hale et al., *Molecular Cell* 45 (3):292-302 (2012); Cong et al., *Science* 339 (6121):819-823 (2013); Mali et al., *Science* 339 (6121):823-826 (2013)).

Gene inactivation, i.e., inhibition of functional expression of the gene, may, for instance, also be achieved through the creation of transgenic organisms expressing antisense RNA, or by administering antisense RNA to the subject. An antisense construct can be delivered, for example, as an expression plasmid, which, when transcribed in the cell, produces RNA that is complementary to at least a unique portion of the cellular NEAT1 lncRNA.

A more rapid method for the inhibition of gene expression is based on the use of shorter antisense oligomers consisting of DNA, or other synthetic structural types such as phosphorothiates, 2'-0-alkylribonucleotide chimeras, locked nucleic acid (LNA), peptide nucleic acid (PNA), or morpholinos. With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. An "antisense oligomer" refers to an antisense molecule or anti-gene agent that comprises an oligomer of at least about 10 nucleotides in length. In some embodiments, an antisense oligomer comprises at least 15, 18, 20, 25, 30, 35, 40, or 50 nucleotides. Antisense approaches involve the design of oligonucleotides (either DNA or RNA, or derivatives thereof) that are complementary to an RNA encoded by polynucleotide sequences of NEAT1. Antisense RNA may be introduced into a cell to inhibit translation of a complementary mRNA by base pairing to it and physically obstructing the translation machinery. This effect is, therefore, stoichiometric. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense oligomers should be at least 10 nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruitflies. RNA interference (RNAi) is a form of post-transcriptional gene silencing. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Several reports describe the same catalytic phenomenon in other organisms, including experiments demonstrating spatial and/or temporal control of gene inactivation, including plant (*Arabidopsis thaliana*), protozoan (*Trypanosoma bruceii*), invertebrate (*Drosophila melanogaster*), and vertebrate species (*Danio rerio* and *Xenopus laevis*). The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) *Nature* 411:494 498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence contained within the target mRNA. The sense and antisense strands of the present siRNA can comprise two complementary, single-stranded RNA molecules or can comprise a single molecule in which two complementary portions are base paired and are covalently linked by a single-stranded "hairpin" area (often referred to as shRNA). The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

The siRNAs of the disclosure can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can also comprise a 3' overhang. A "3' overhang" refers to at least one unpaired nucleotide extending from the 3' end of an RNA strand. Thus, in one embodiment, the siRNA of the disclosure comprises at least one 3' overhang of from one to about six nucleotides (which includes ribonucleotides or deoxynucleotides) in length, preferably from one to about five nucleotides in length, more preferably, from one to about four nucleotides in length, and particularly preferably, from about one to about four nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides.

Alternatively, substitution of pyrimidine nucleotides by modified analogues, e.g., substitution of uridine nucleotides in the 3' overhangs with 2' deoxythymidine, is tolerated and does not affect the efficiency of RNAi degradation. In particular, the absence of a 2' hydroxyl in the 2' deoxythymidine significantly enhances the nuclease resistance of the 3' overhang in tissue culture medium.

The siRNAs of the disclosure can be targeted to any stretch of approximately 19 to 25 contiguous nucleotides in any of the target NEAT1 RNA sequences (the "target sequence"), of which examples are given in the application. Techniques for selecting target sequences for siRNA are well known in the art. Thus, the sense strand of the present siRNA comprises a nucleotide sequence identical to any contiguous stretch of about 19 to about 25 nucleotides in the target mRNA.

The siRNAs of the disclosure can be obtained using a number of techniques known to those of skill in the art. For example, the siRNAs can be chemically synthesized or recombinantly produced using methods known in the art. Preferably, the siRNA of the disclosure are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the disclosure from a plasmid include, for example, the U6 or H1 RNA pol III promoter sequences and the cytomegalovirus promoter. Selection of other suitable promoters is within the skill in the art. The recombinant plasmids of the disclosure can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g., in breast tissue or in neurons.

The siRNAs of the disclosure can also be expressed intracellularly from recombinant viral vectors. The recombinant viral vectors comprise sequences encoding the siRNAs of the disclosure and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the disclosure can also comprise inducible or regulatable promoters for expression of the siRNA in the tissue where the tumor is localized.

As used herein, an "effective amount" of the siRNA is an amount sufficient to cause RNAi-mediated degradation of the target mRNA, or an amount sufficient to inhibit the progression of metastasis in a subject. RNAi-mediated degradation of the target mRNA can be detected by measuring levels of the target mRNA or protein in the cells of a subject, using standard techniques for isolating and quantifying mRNA or protein as described above.

One skilled in the art can readily determine an effective amount of the siRNA of the disclosure to be administered to a given subject, by taking into account factors such as the size and weight of the subject; the extent of the disease penetration; the age, health and sex of the subject; the route of administration; and whether the administration is regional or systemic. Generally, an effective amount of the siRNA of the disclosure comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

It has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers, therefore, represent an important new class of antisense molecule. Oligomers of the disclosure may be synthesized by standard methods known in the art. As examples, phosphorothioate oligomers may be synthesized by the method of Stein et al. (1988), Nucleic Acids Res. 16:3209 3021), methylphosphonate oligomers can be prepared by use of controlled pore glass polymer supports (Sarin et al. (1988), *Proc. Natl. Acad. Sci. U.S.A.* 85:7448-7451). Morpholino oligomers may be synthesized by the method of Summerton and Weller, U.S. Pat. Nos. 5,217,866 and 5,185,444.

Another particular form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H-mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects, together with non-specific binding causing off-target effects, has stimulated the design of new artificial nucleic acids for the development of modified oligonucleotides that provide efficient and specific antisense activity in vivo without exhibiting toxic side-effects. By recruiting RNase H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g., LNA™ longRNA GapmeRs by Exiqon, or MOE Gapmers by Isis pharmaceuticals. MOE gapmers or "2'MOE Gapmers" are an antisense phosphorothioate oligonucleotide of 15-30 nucleotides, wherein all of the backbone linkages are modified by adding a sulfur at the non-bridging oxygen (phosphorothioate) and a stretch of at least ten consecutive nucleotides remain unmodified (deoxy sugars) and the remaining nucleotides contain an O'-methyl O'-ethyl substitution at the 2' position (MOE). Exemplary gapmers for NEAT1 inhibition are listed in the Examples.

According to a further aspect, the inhibitors of functional expression of NEAT1 are provided for use as a medicament. According to yet further aspects, the inhibitors of functional expression of NEAT1 are provided for use in treatment of cancer, in particular, for use in treatment of solid tumors. In still further embodiments, the inhibitors are provided for use in treatment of carcinoma (epithelial cancers).

Typical examples of carcinomas include, but are not limited to: epithelial neoplasms (ICD 8010-8045), squamous cell neoplasms (ICD 8050-8080), such as squamous cell carcinoma, basal cell neoplasms (ICD 8090-8110), such as basal cell carcinoma, transitional cell carcinomas (ICD 8120-8130), adenocarcinomas (ICD 8140-8380), such as adenocarcinoma, linitis plastic, vipoma, cholangiocarcinoma, hepatocellular carcinoma, adenoid cystic carcinoma, renal cell carcinoma, adnexal and skin appendage neoplasms (ICD 8390-8420), mucoepidermoid neoplasms (ICD 8430-8439), cystic, mucinous and serous neoplasms (ICD 8440-8490), ductal, lobular and medullary neoplasms (ICD 8500-8540), acinar cell neoplasms (ICD 8550-8559), and complex epithelial neoplasms (ICD 8560-8580).

Examples of organ sites of carcinomas include, but are not limited to, lung, breast, prostate, colon and rectum, pancreas and ovaries.

According to alternative embodiments, the inhibitors are provided for use in treatment of cancers selected from the group of breast cancer, skin cancer, osteosarcoma, colorectal cancer, and neuroblastoma. According to very specific embodiments, the skin cancer is non-melanoma skin cancer. According to further specific embodiments, the skin cancer is selected from BCC or SCC.

According to very specific embodiments, the cancer envisaged for treatment is not a blood tumor. For example, the cancer is not selected from the group consisting of leukemia, lymphoma and multiple myeloma. Blood tumors (or liquid tumors) are typically characterized by chromosomal translocations that are not often observed in solid tumors, leading to different diagnosis and treatment paradigms. Also, as these tumor cells typically circulate, local administration of therapy is much more difficult.

According to similar embodiments, methods of treating cancer in a subject in need thereof are provided, comprising administering an inhibitor of functional expression of NEAT1 to the subject. Here also, particularly envisaged cancers to be treated are solid tumors. In still further embodiments, methods are provided for treating carcinoma in a subject in need thereof. The cancers to be treated are as elaborated above.

The nature of the NEAT1 inhibitor is not vital to the disclosure, as long as it inhibits the functional expression of the NEAT1 gene. According to specific embodiments, the inhibitor is selected from an inhibitory RNA technology (such as a gapmer, an shRNA, an siRNA), a CRISPR, a TALEN, or a Zinc-finger nuclease. According to specific embodiments, the inhibitor is administered to, or is targeted to, cancer cells (such as solid tumor cells).

According to alternative, but not exclusive, specific embodiments, the inhibitor selectively induces apoptosis in cancer cells. This particularly implies that it induces apoptosis in cancer cells, but not in normal (non-transformed) similar cells. Similar in this context means cells from the same tissue or origin, but non-transformed, e.g., epithelial cells as compared to carcinoma cells.

According to further specific embodiments, the inhibitor induces apoptosis independent of p53 status, e.g., independent whether p53 has particular mutations or not, or independent of its expression levels.

Although inhibition of NEAT1 expression is enough to induce apoptosis of cancer cells (see Examples section), combination treatments of NEAT1 inhibitors with other anti-cancer agents are envisaged as well. As NEAT1 inhibition interferes with DNA repair pathways (particularly the homologous recombination and non-homologous end-joining repair pathways), particularly envisaged combinations are with inhibitors of other repair pathways, such as the base excision repair pathway.

Thus, according to particular embodiments, combinations of an inhibitor of a DNA excision repair enzyme with an inhibitor of functional expression of NEAT1 are provided for use in the treatment of cancer. Likewise, methods for treating cancer are provided to treat a subject in need thereof, in which a combination of an inhibitor of a DNA excision repair enzyme with an inhibitor of functional expression of NEAT1 is administered to the subject.

According to a further aspect, methods are provided that may identify whether a cancer is suitable for treatment with an inhibitor of functional expression of NEAT1. These methods typically have the following steps:
  Determining whether expression of NEAT1 is increased in the cancer or a sample of cancer cells; and
  Establishing whether the tumor is suitable for treatment, wherein increased expression is indicative of suitability for treatment.

"Determining expression" may encompass processes such as detecting or measuring the presence of gene products, or determining the expression levels, i.e., the (relative or absolute) amount of gene product present. Determining expression may be done qualitatively (i.e., whether or not there is expression in a sample) and/or quantitatively (determining the amount of expression, or expression levels). Most typically, expression will be done quantitatively, in order to be able to compare expression levels. Determining expression may involve comparison with a positive control (e.g., to assess whether gene products can be detected in the sample, in particular, whether the detection method works), a negative control or a blank (typically to assess whether no false positive signal is being generated), one or more standards (either internal or external standards, typically to allow more accurate quantification), or a combination thereof. The positive control may additionally or alternatively be an internal positive control, typically a gene product known to be present in the sample (e.g., to assess whether gene products can be detected in the sample, in particular, whether the detection method works or whether gene products are indeed present in the sample). Detection of expression and/or activity is well known in the art, and a skilled person is capable of choosing appropriate controls and/or standards.

Note that determining the presence or expression of NEAT1 means determining presence or expression of at least one isoform. It is explicitly envisaged to determine presence or expression of the total of all RNA isoforms of NEAT1, or one or more specific RNAs.

As mentioned, determining the amount of a gene may involve comparison with one or more controls or standards. Typically, this will be done to establish whether the levels of the gene product are altered, most particularly increased. As used herein, "altered levels" of a gene product may mean either "increased levels" or "decreased levels" of a gene product, which is typically assessed versus a control. The skilled person is capable of picking the most relevant control. This may, for instance, depend on the particular gene product, the nature of the cancer studied, the sample(s) that is/are available, and so on. Suitable controls include, but are not limited to, expression in cells of a subject that is cancer-free (optionally from the same subject when he/she was still healthy), or a set of clinical data on average gene product levels in healthy volunteers. It may also be an artificially generated expression standard, e.g., as used in "real" quantitative PCR. As is evident from the foregoing, the control may be from the same subject or from one or more different subjects or derived from clinical data. Optionally, the control is matched for, e.g., sex, age, etc.

With "increased levels of a gene product," as mentioned herein, is meant levels that are higher than are normally present. Typically, this can be assessed by comparing to the control. According to particular embodiments, increased levels of a gene product are levels that are 10%, 20%, 25%, 30%, 40%, 50%, 60%, 70%, 75%, 80%, 90%, or even up to 100% higher than those of the control. According to further particular embodiments, it means that the gene product is present, whereas it normally (or in control) is absent, or at virtually non-detectable levels. In other words, in these embodiments, detecting the presence of a particular gene product is equivalent to detecting increased levels of the gene product. According to yet further particular embodiments, it means that the gene product is present, whereas in the majority of cell samples from tumor-free individuals, taken as a control, it is not. The skilled person will appreciate that the exact levels by which a gene product needs to be higher in order to allow a reliable and reproducible diagnosis may depend on the type of tumor tested, of which isoform the levels are assessed and the natural variability of these levels. However, assessing the increase itself is fairly straightforward, since it only requires routine techniques.

Instead of looking at increased levels compared to a control with normal levels, the skilled person will appreciate that an alternative, comparing to a control with high levels (e.g., a sample of a tumor in which NEAT1 is highly expressed), can also be done. Thus, if the gene product levels measured in the cells or cell sample are similar to those of a suitable "control" obtained from a subject with a tumor sensitive to treatment with NEAT1 inhibitors, this may be considered equivalent to increased gene product levels compared to a positive control, and be correlated to sensitivity of the cells to treatment with inhibitors of functional NEAT1 expression. In the other case, if gene product levels are significantly lower than those of a control with high levels of NEAT1, this can be used to establish insensitivity to treatment with inhibitors of DNA base excision repair enzymes.

For "decreased levels" of a gene product compared to a positive or negative control, the considerations about increased levels of a gene product apply mutatis mutandis. Of course, gene product levels may be compared to both a negative and a positive control in order to increase accuracy of the diagnosis.

Assessing decreased levels of NEAT1 can, e.g., be done to monitor the success of NEAT1 inhibition, to check whether the therapy is successful.

According to particular embodiments, determining the expression (or the increased expression) of NEAT1 is done by determining the expression of the long isoform of NEAT1.

Of note, since NEAT1 is a major structural component of paraspeckles, determining the expression of NEAT1 can be done by assessing the presence and/or the number of paraspeckles in the cells of the sample. An increase in number of paraspeckles is equivalent to an increase in functional NEAT1 expression, whereas a decrease (or absence) of paraspeckles indicates decreased expression of NEAT1.

As the methods comprise a step of determining expression of NEAT1 in the cancer or a sample of cancer cells, the methods thus may entail a first step of providing a sample of cancer cells. The determining step may occur purely in vitro, i.e., without a step interacting on the human or animal body.

According to particular embodiments, the cancer is a solid tumor. According to alternative embodiments, the tumor is a carcinoma. According to further alternative embodiments, the cancer is selected from breast cancer, skin cancer, osteosarcoma, colorectal cancer, and neuroblastoma.

According to specific embodiments, when it is established that the tumor is suitable for treatment, the methods may further comprise a step of administering an inhibitor of functional expression of NEAT1 to the subject in which the tumor is present in order to treat the tumor.

As already mentioned, the NEAT1 expression levels can be monitored after administration of the inhibitor to check whether the functional expression of NEAT1 decreases (typically compared to the situation prior to treatment). This can be correlated to success of the therapy.

According to alternative particular embodiments, the methods may comprise a step of administering a combination of an inhibitor of functional expression of NEAT1 and an inhibitor of a base excision repair enzyme, such as a PARP inhibitor.

It is to be understood that although particular embodiments, specific configurations as well as materials and/or molecules, have been discussed herein for cells and methods according to this disclosure, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

NEAT is a Direct Target Gene of p53, and it is Induced in Different Cell Types

By performing RNAseq and ChIPseq analysis, NEAT1 was confirmed as a direct target gene of p53 (FIG. 1).

Treatment of the breast cancer cell line MCF-7 with Nutlin3A, a specific antagonist of the master negative regulator of p53, MDM2, transcription of NEAT1, and particularly the long isoform NEAT1_2, is upregulated as illustrated by the increased intensity of the RNA-seq peaks (in blue in FIG. 1). This upregulation is mediated through the recruitment of p53 to the NEAT1 promoter as illustrated by the increase intensity of the p53-ChIP-seq peaks (green in FIG. 1).

Figure 2A:
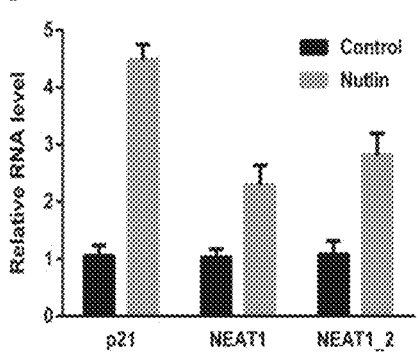
FIGS. 2A-2G. Both NEAT1 transcripts (NEAT1_1 and the long isoform NEAT1_2) are induced by Nutlin3a in various p53 wild-type human cancer cell lines. The effect is p53-dependent.
Figure 2B:
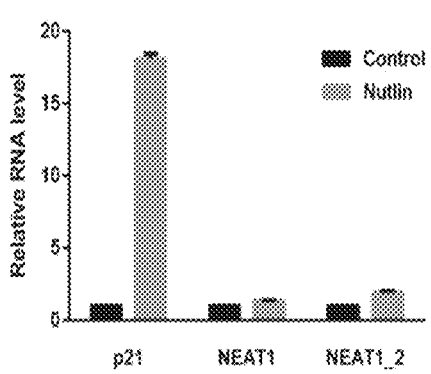
Figure 2C:
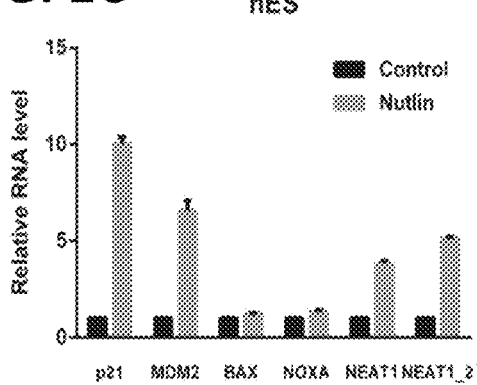
Figure 2D:
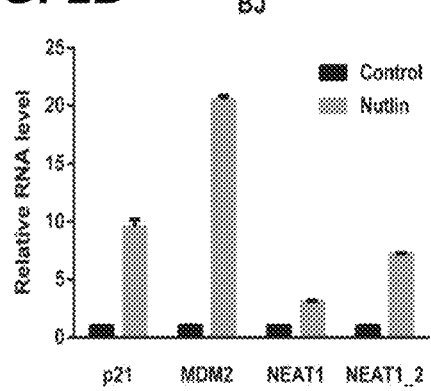

The effect of Nutlin3A on NEAT1 expression was evaluated in several other cell lines, including U2OS (osteosarcoma, FIG. 2A), A459 (lung carcinoma, FIG. 2B), human ES cells (FIG. 2C), and an immortalized human fibroblast cell line (BJ, FIG. 2D). p21, a p53 target gene was used as control, as this should be upregulated by Nutlin3A exposure. It could be shown that Nutlin3A indeed induces expression of NEAT1 in these different cell lines. Both isoforms are affected, with the effect being stronger for the longer isoform (NEAT1_2).

Figure 2E:
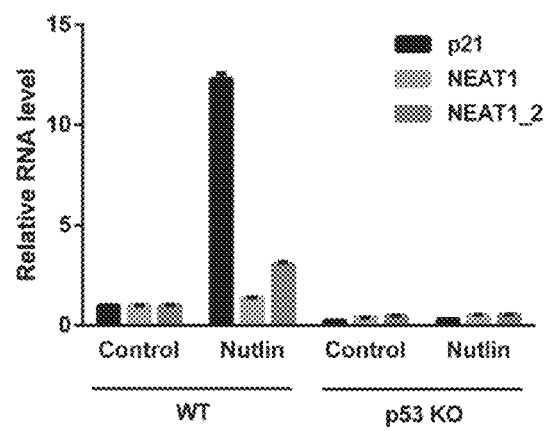
Figure 2F:
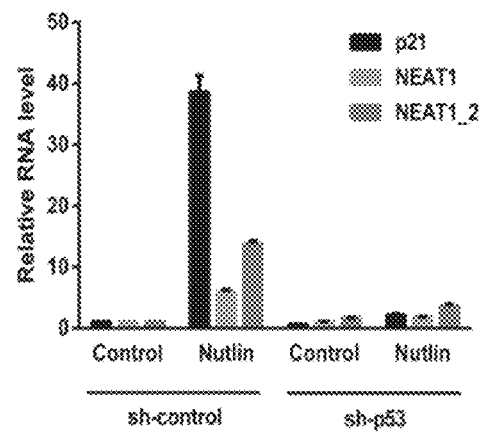
Figure 2G:
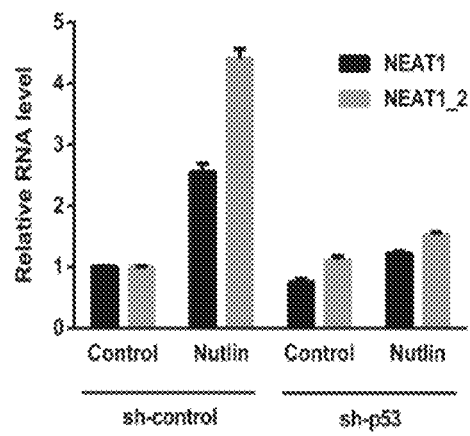

Next, it was evaluated whether this effect is p53-dependent. Knocking down p53 in MCF-7 by shRNA (p53 shRNA sequence: GACTCCAGTGGTAATCTACTTCAAGA-GAGTAGATTACCACTGGAGTCTTTTTT; SEQ ID NO: 1) abolishes the upregulation of NEAT1, indicating that Nutlin-mediated NEAT1 induction is indeed p53-dependent (FIG. 2F). Comparable results were obtained in a Neuroblastoma cell line (NGP; FIG. 2G).

Thus, the induction of NEAT1 is both p53-dependent and not limited to breast cancer cell lines.

To differentiate between the different isoforms of NEAT, the following strategy was used. All qPCRs labeled NEAT1 or NEAT1_1 were done with primers targeting the region of +/−2200 bp. The knock-down probes labeled as such also target the region between 2000 and 3756 bp. The RNA-FISH probeset used is made up of a large set of oligos targeting region 1-3756 bp. The primers and knock-down probes labeled NEAT1_2 (the long transcript) target a region of +/−21300 bp. The RNA-FISH probes (again a set of oligos) target the portion from 3800-11700 bp to avoid detection of shorter isoforms.

The gapmers used to inhibit NEAT1 were the following:

```
NEAT1-Gapmer4
                          (SEQ ID NO: 2)
GACGTAACAGAATT

NEAT1-Gapmer5
                          (SEQ ID NO: 3)
TAAGCACTTTGGAAAG

NEAT1-Gapmer6
                          (SEQ ID NO: 4)
CTCACACGTCCATCT
```

Gapmers 4 and 5 inhibit both the long and short isoform of NEAT1; gapmer 6 is specific for the long isoform.

NEAT1 induction in response to Nutlin can be seen in the colorectal cancer cell line HCT116, but not in an isogenic p53 KO HCT116 cell line (FIG. 2E), again confirming that the nutlin-induced expression of NEAT1 is p53-mediated. The p53-NEAT1 pathway is also conserved in the mouse as Nutlin induces expression of NEAT1 in early passage (P3) mouse embryonic fibroblasts (MEFs) (not shown).

Figure 3A:
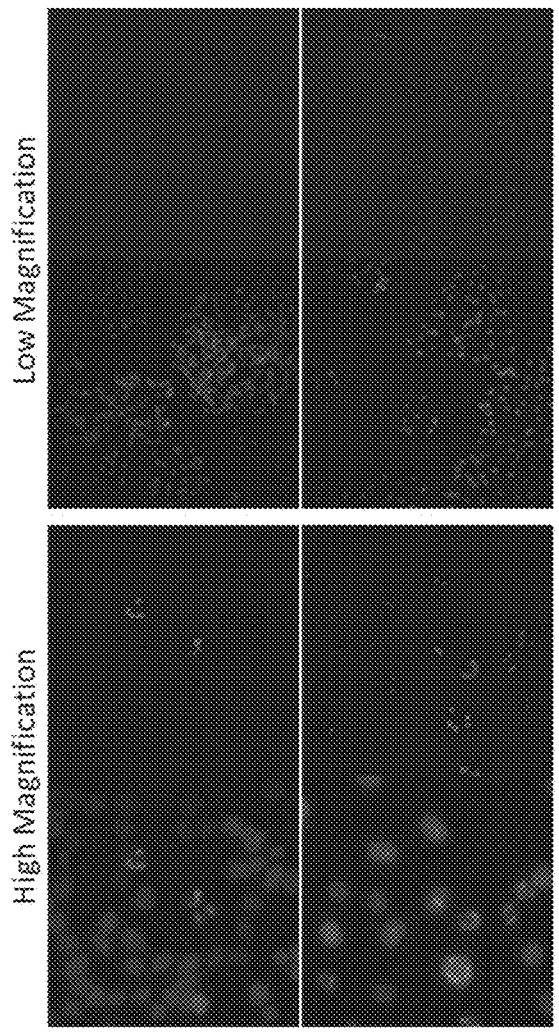
FIGS. 3A and 3B. Nutlin3a induces paraspeckles formation in a p53-dependent manner.
Figure 3B:
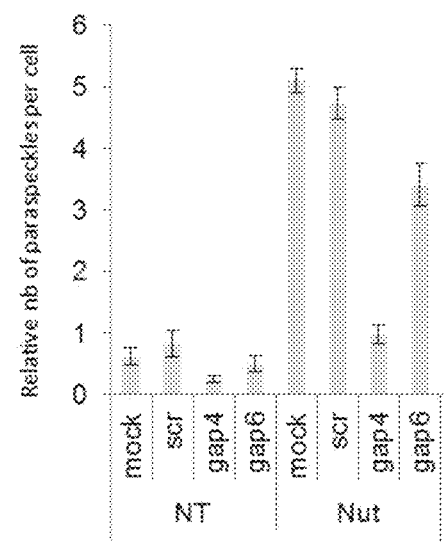

The upregulation of NEAT1 by Nutlin also has functional consequences: Nutlin induces paraspeckles formation in MCF-7 cells (FIGS. 3A and 3B).

Paraspeckles (red) are detected by RNA-FISH in the nuclei (blue; DAPI staining) of MCF-7 following Nutlin exposure; the effect is dramatically attenuated when NEAT1 (both isoforms or only long isoform) is inhibited (FIGS. 3A and 3B, images treated with gapmer 4 or 6). The relative number of paraspeckles per cell for non-treated (NT) or Nutlin3a-treated cells is shown in FIG. 3B. A similar observation in MCF-7 cells treated with p53 shRNA confirms again that this induction is p53-dependent (data not shown). Thus, p53 stimulates the formation of paraspeckles in these cells.

A comparable result has been obtained in the immortalized human diploid fibroblast cell line, BJ (data not shown). Transfection of the cells with LNA-gapmers 4 and 6, both targeting NEAT1, also decrease the formation of paraspeckles, confirming previous studies showing that paraspeckles formation is dependent on the expression of NEAT1.

Example 2

NEAT1 is Induced by Different Forms of Low and/or Chronic Stress, but not by High Stress The data indicate that whereas a clear p53-dependent induction of NEAT1 and paraspeckles formation is observed in response to low/chronic stress levels, no induction is seen in response to acute stress levels (FIGS. 4A-4F).

NEAT1 is upregulated in different conditions of low chronic stress: it is induced in the melanoma cells Mel 501 undergoing senescence in response to exposure to the aurora kinase inhibitor, AZD (FIG. 4A); it is induced in BJ cells in response to oxidative stress induced by exposure of the cells to rotenone (FIG. 4B); it is also induced in response to low dose of Doxorubicin (FIG. 4C) and during replication stress (RS) in the Wi38 (lung fibroblast) cell line (FIG. 4D) and mouse NEAT1 in induced in MEFs upon passages in culture (data not shown). It has been shown that p53 is induced in MEFs during passages as a response to increasing oxidative stress levels generated by culturing of the cells in normoxic conditions. As a side note, NEAT1 is also found upregulated in pigmented/thickened epidermal keratinocytes, an epithelial cell type (not shown). This is in line with chronic stress caused by UV radiation.

Figure 4A:
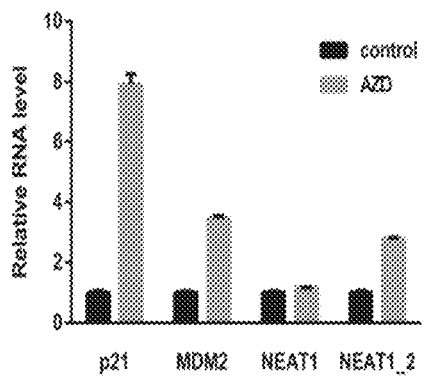
FIGS. 4A-4F. NEAT1 is induced in human and mouse cells exposed to low stress conditions including exposure to the inducer of senescence aurora-kinase inhibitor AZD1152-HQPA (AZD.
Figure 4B:
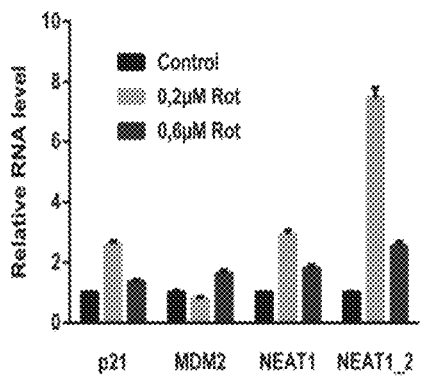
Figure 4C:
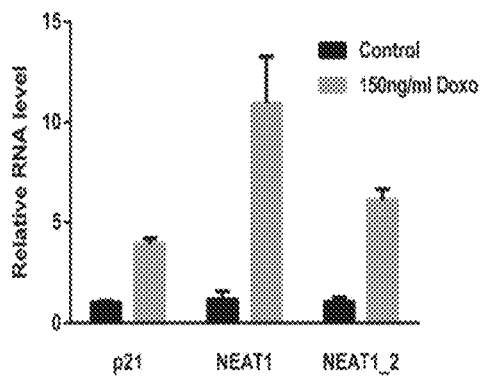
Figure 4D:
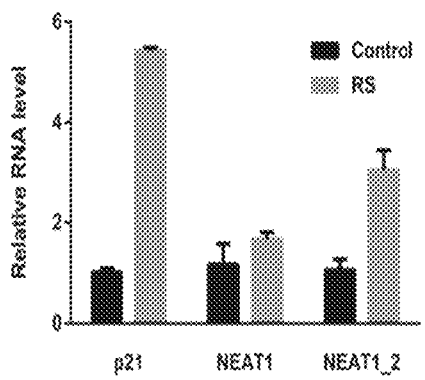
Figure 4E:
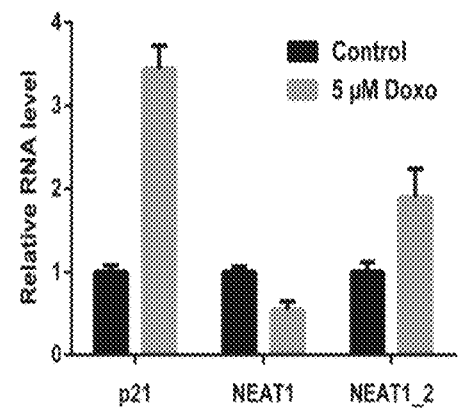
Figure 4F:
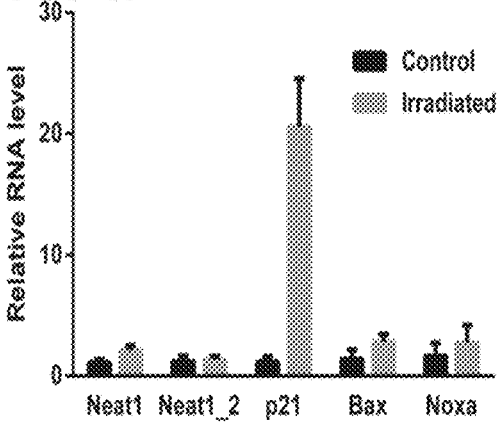

Remarkably, the induction of NEAT1 expression occurs only in response to low dose of doxorubicin, but not significantly to higher dose (5 µM, FIG. 4E). The same is true for cells that are exposed to high doses of irradiation (FIG. 4F).

Figure 5:
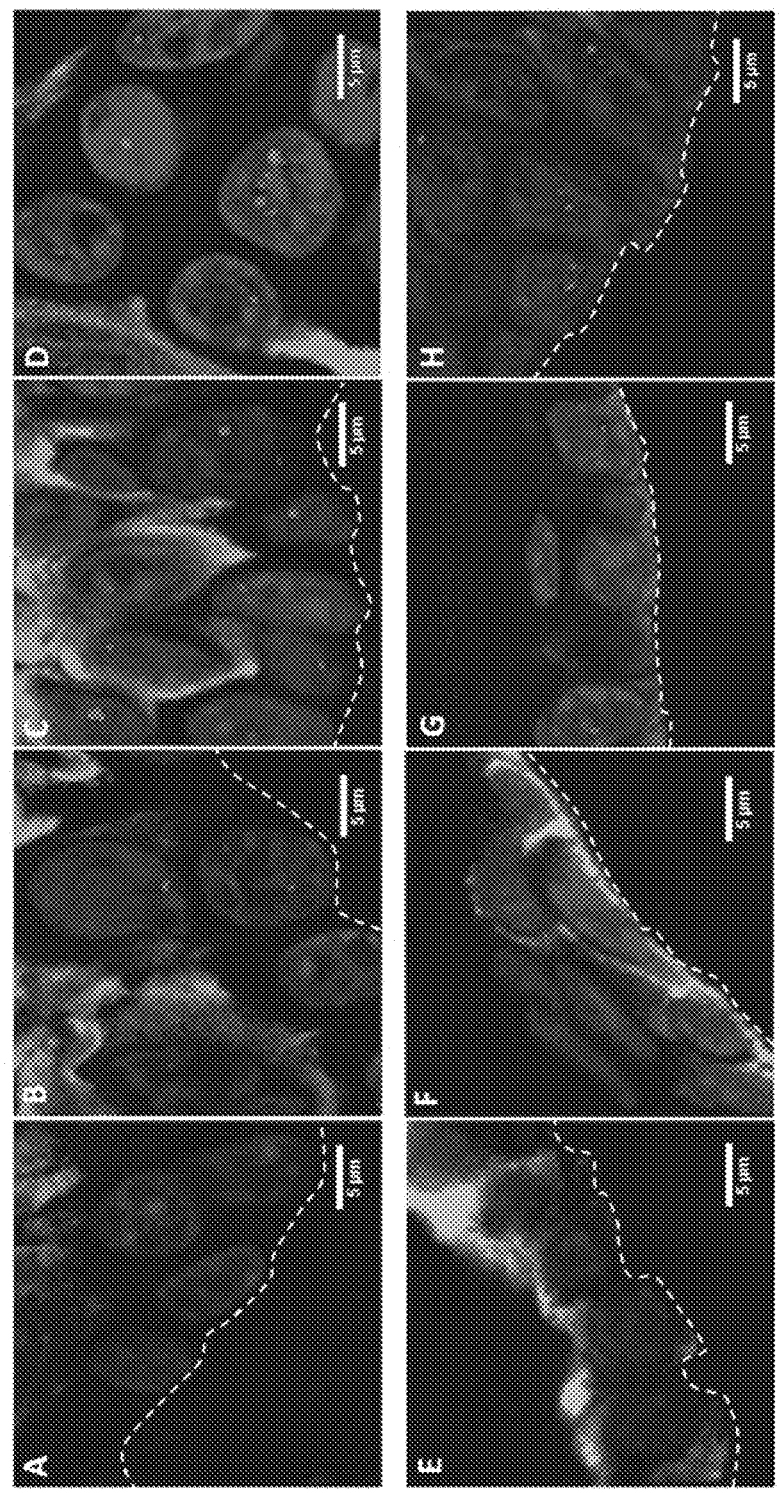
FIG. 5. NEAT1 paraspeckles are formed in vivo in response to oncogenic stress. Panels A-D: Paraspeckles form upon oncogenic stress after DMBA/TPA treatment. Nuclear staining with DAPI (blue), staining of the paraspeckles using RNA-FISH of NEAT1 (red), and co-staining of the suprabasal layers of the epidermis with Keratin 1 (green). White dotted lines delineate the basement membrane of the epidermis. No paraspeckles are observed in normal epidermis 48 hours after topical DMBA treatment (Panel A). Paraspeckles are present and gradually more abundant in interfollicular epidermis hyperplasia (Panel B), epidermal papilloma (Panel C) and differentiated squamous cell carcinoma (Panel D). Panels E-H: Paraspeckles form upon oncogenic stress in the K19 CreER KRasLSL-G12D genetic mouse model (Lapouge et al., 2011). Nuclear staining with DAPI (blue), staining of the paraspeckles using RNA-FISH of NEAT1 (red) and co-staining of the basal and suprabasal layers of the epidermis with Keratin 5 (cyan). White dotted lines delineate the basement membrane of the epidermis. Staining of the epidermis is shown, 1 week (Panel E), 1 month (Panel F) and 2 months (Panel G) after Tamoxifen administration or upon occurrence of epidermis hyperplasia, and 4 months after Tamoxifen administration (Panel H).

Apart from low and chronic stress, the effect of oncogenic stress was evaluated by treatment with DMBA/TPA (7,12-Dimethylbenz[a]anthracene and 12-O-tetradecanoylphorbol-13-acetate) as carcinogens (FIG. 5).

Example 3

Generation of NEAT1 KO Mice Shows that they do not have Major Growth Defects

To examine the physiological role of NEAT1 and paraspeckles in vivo, mice that lack NEAT1 were generated. In line with an earlier report (Nakagawa et al., 2011), NEAT1 knock-out (KO) mice are viable and have no immediate apparent phenotype. However, we observed a defect in pubertal mammary gland branching morphogenesis along with reduced lobular-alveolar development during pregnancy and lactation capacity (data not shown). See Standaert et al., *RNA*, 2014 for a complete description of this work.

Example 4

Figure 6A:
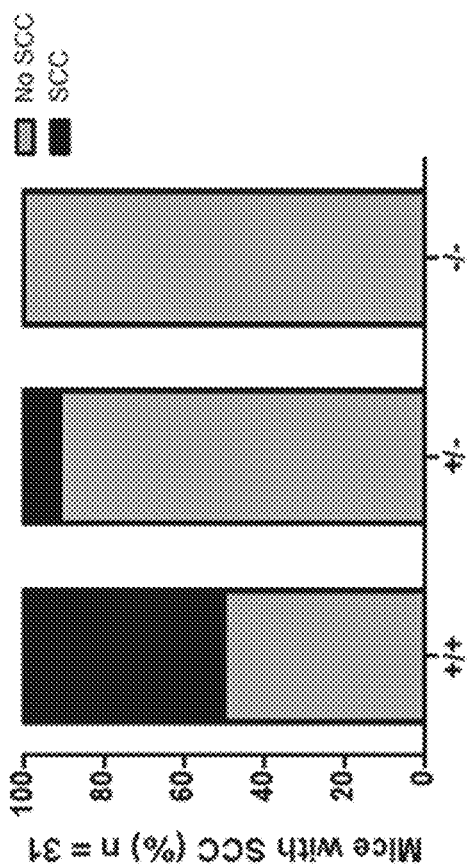
Figure 6B:
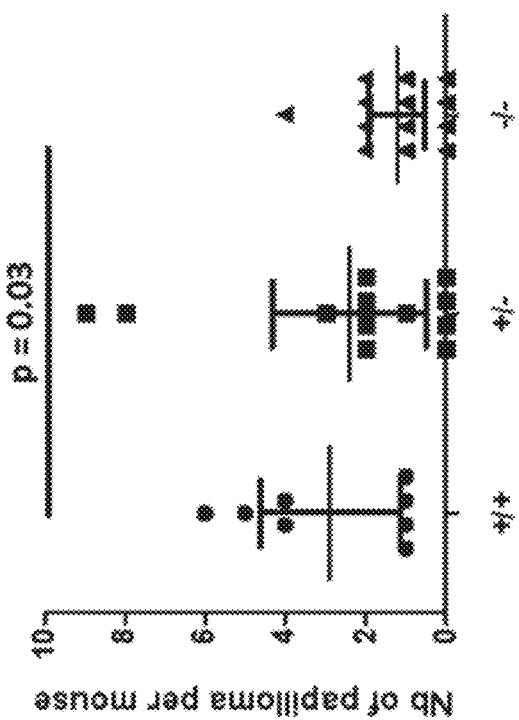
Figure 7C:
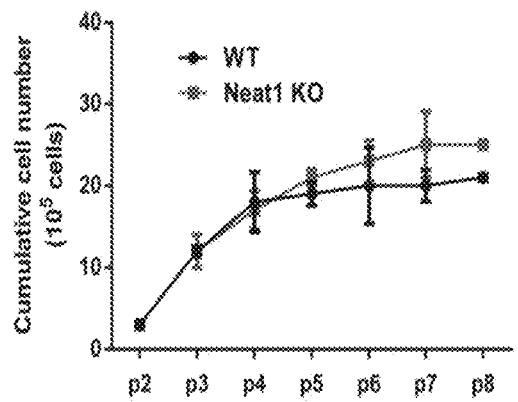
Figure 7D:
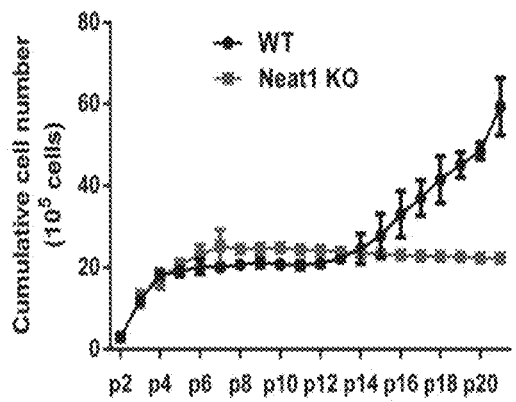
Figure 7E:
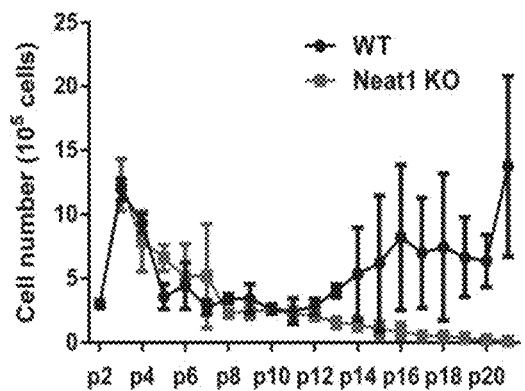
Figure 7F:
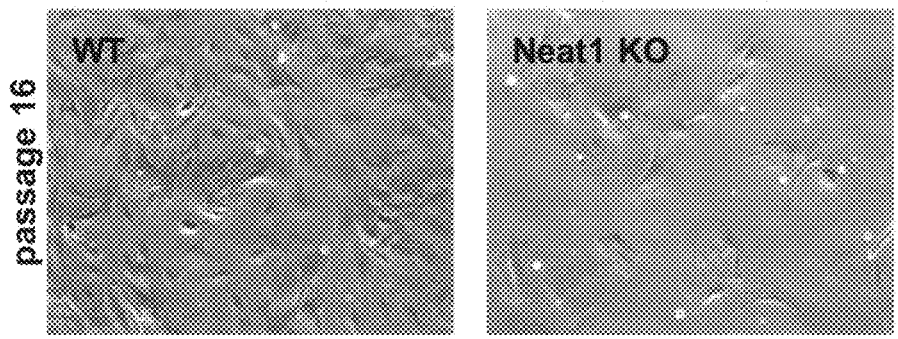

NEAT1 Inhibition Selectively Affects Survival of Cancer, but not of Normal Cells Although NEAT1 KO mice show no apparent growth defects, tumor development is significantly altered in NEAT1 KO (−/−) mice exposed to a two-stage chemically induced carcinogenesis protocol (DMBA/TPA). NEAT1 inhibition results in significantly less papilloma formation in this model (FIGS. 6A-6C). Heterozygous (NEAT1+/−) mice show an intermediate phenotype.

To further study the effect of loss of NEAT1 on cell growth and survival, NEAT1 KO MEFs were explanted in culture. These cells show no overall growth defect at early passages and enter senescence just like their WT counterparts. Remarkably, however, the NEAT1 KO cells eventually die (after many passages in culture) and cannot be immortalized, in contrast to the WT MEFs (FIGS. 7A-7F). This indicates that NEAT1 has a pro-survival function in chronic stress culture conditions, and that its inhibition induces apoptosis when cells accumulate, possibly immortalizing/transforming mutations. Since immortalization of MEFs is invariably associated with inactivation of the p53 pathway, this result indicates that NEAT1 and p53 may be synthetically lethal.

Figure 9A:
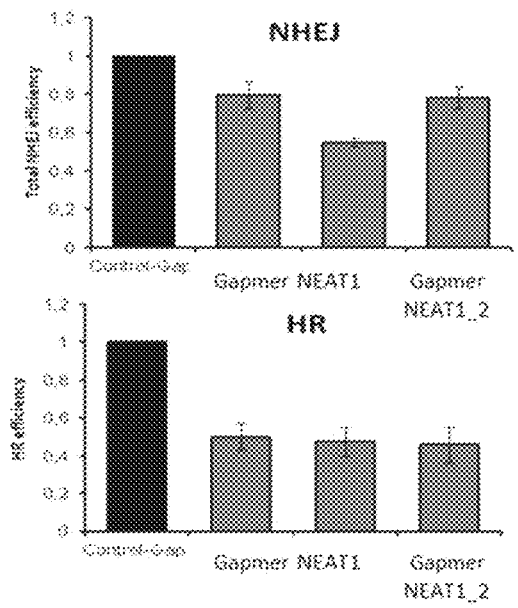
FIGS. 9A-9C. Knock-down of NEAT1 impairs HR and NHEJ DNA repair (FIG. 9A) but not Alt-NHEJ or SSA (FIG. 9B).
Figure 9B:
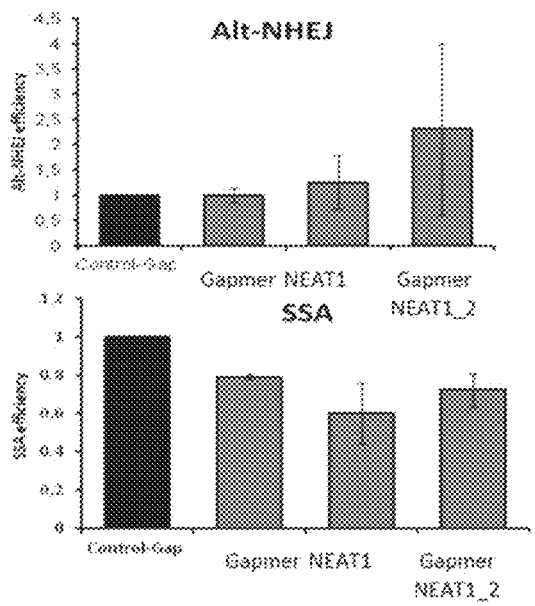
Figure 9C:
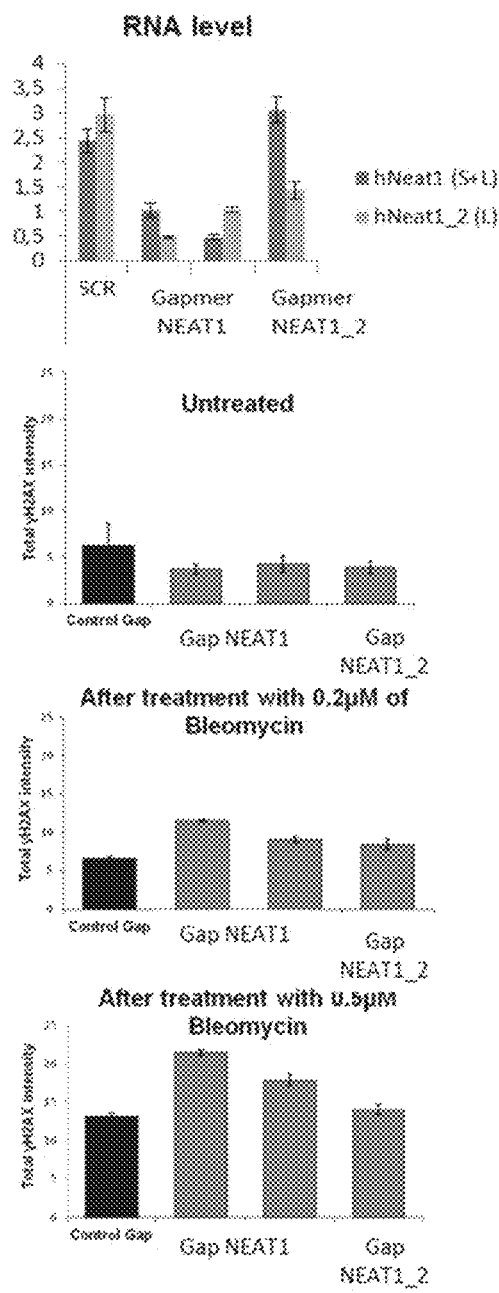

To further extend the anti-oncogenic effects observed in NEAT1 KO mice, NEAT1 was inhibited in different cancer cells using LNA-gapmers. These different gapmers can efficiently knockdown NEAT1 (either both long and short isoforms (gap 4, gap 5) or only the long isoform (gap 6). The KD efficiency of these gapmers are illustrated in FIGS. 8A and 9C. It could be shown that, in different cancer cell types, NEAT1 KD induces paraspeckles (FIG. 8B), reduces cell viability and induces apoptosis, as measured by increased caspase 3 and 7 activity and FACS analysis (FIG. 8C). Metabolic activity of cancer cells and thus growth is also severely affected (FIG. 8D). For U2OS cells, detachment of the cells from their plastic support was observed (data not shown).

Example 5

NEAT1 Inhibition Impairs DNA Repair Pathways and Mitochondrial Fission, and Sensitizes Cancer Cells to p53 Reactivation Therapy One of the possible mechanisms underlying the NEAT1-induced cellular survival is activation of DNA repair. Thus, effect of NEAT1 inhibition on DNA repair pathways was evaluated. It was found that knock-down of NEAT1 impairs HR and NHEJ DNA repair (FIG. 9A), but not Alt-NHEJ or SSA repair (FIG. 9B). Consequently, additional inhibition of the non-inhibited, base excision repair (BER) pathway will give rise to synthetic lethality.

To confirm the hypothesis that NEAT1 inhibition interferes with DNA repair, U2OS cells were exposed to different concentrations of the DNA-damaging agent bleomycin. In NEAT1-inhibited cells, DNA damage (as measured by γH2AX intensity) is indeed increased (FIG. 9C, last three panels). Thus, DNA repair is severely impaired in NEAT1 KD cells. Of note, the longest transcript is about 8× less expressed than the shorter forms; thus, it is expected that NEAT1_2 gapmer does not lead to KD when detecting expression with NEAT1 primers, since KD efficiency of gapmerNEAT1_2 is about 50%) (NEAT1=hNeat1; NEAT1_2=hNeat1_2).

Figure 10A:
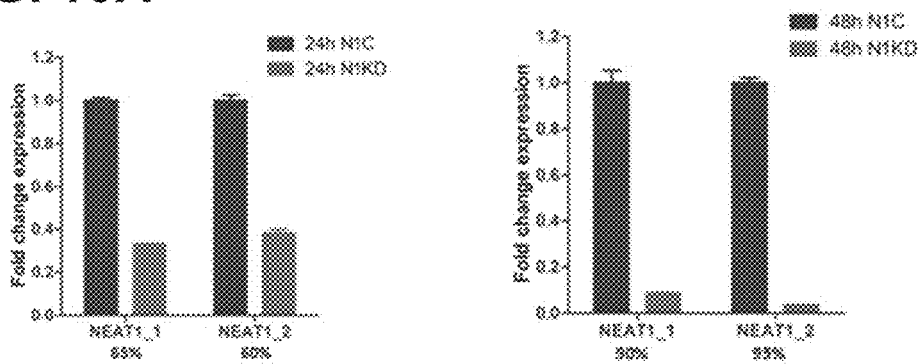
FIGS. 10A and 10B. NEAT1 KD leads to a dramatic decrease in MFF expression.
Figure 10B:
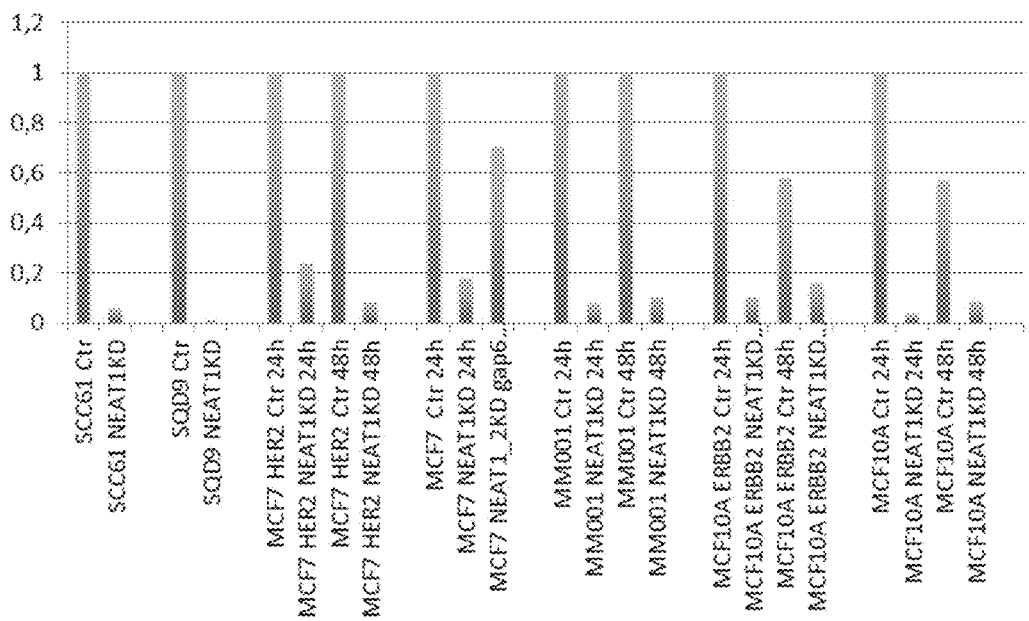

Another mechanism that may underlie the apoptotic effects observed upon NEAT1 inhibition are mitochondrial defects, as NEAT1 and the associated paraspeckles control mitochondria dynamics. It could be observed that NEAT1 inhibition leads to a dramatic decrease in MFF (Mitochondrial fission factor) expression (FIGS. 10A and 10B).

Figure 11A:
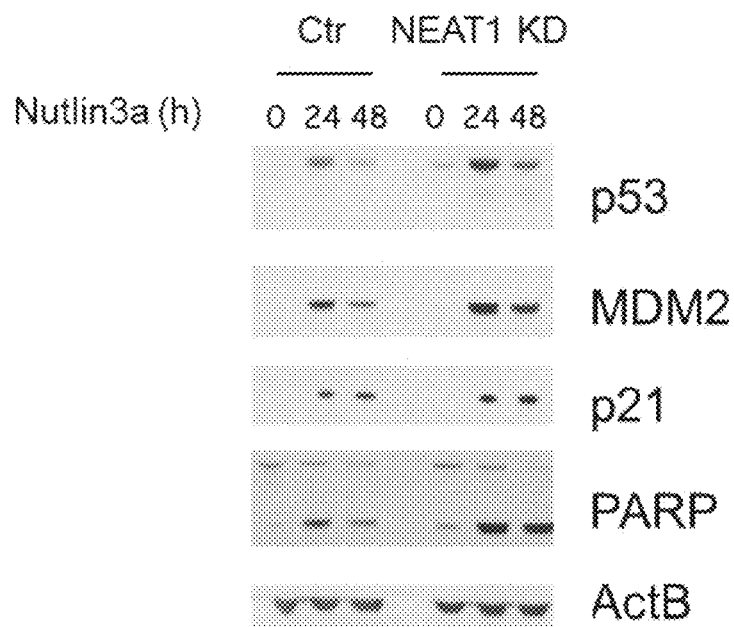
FIGS. 11A and 11B. NEAT1 KD in cancer cells leads to an increase in basal p53 activity and sensitizes p53 wild-type cancer cells to p53 reactivation therapy.
Figure 11B:

Further, NEAT1 KD leads to an increase in basal p53 activity, as shown by Western blot (FIG. 11A) and by induction of p53 transcriptional activity (FIG. 11B).

Figure 12:
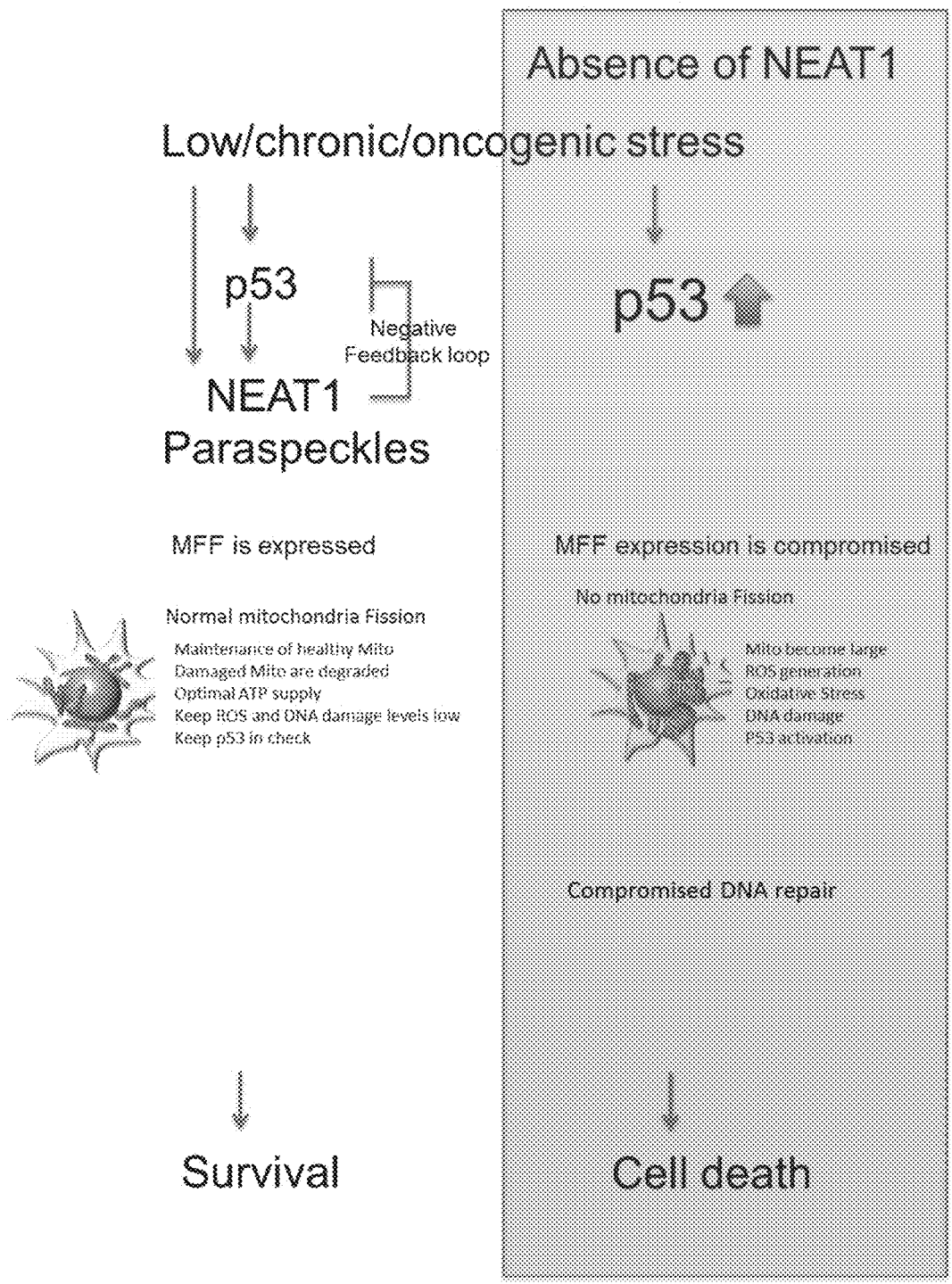
FIG. 12. Model of how NEAT1 upregulation in response to low, chronic and/or oncogenic stress contributes to cell survival in pre-neoplastic cells. When exposed to the same stress, cells that lack NEAT1 will die as a result of mitochondrial defects and compromised DNA repair.

Thus, a model is proposed (FIG. 12) in which NEAT1 helps cellular survival (e.g., of pre-neoplastic cells) by keeping normal mitochondrial fission, DNA damage and p53 in check in response to low/chronic or oncogenic stress. Loss of NEAT1 severely compromises the viability of pre-neoplastic cells in response to these stress conditions.

REFERENCES

Nakagawa S., T. Naganuma, G. Shioi, and T. Hirose. Paraspeckles are subpopulation-specific nuclear bodies that are not essential in mice. *J. Cell. Biol.* 2011; 193(1): 31-9.

Standaert L., C. Adriaens, E. Radaelli, A. Van Keymeulen, C. Blanpain, T. Hirose, S. Nakagawa, and J. C. Marine. The long noncoding RNA Neat1 is required for mammary gland development and lactation. *RNA* 2014 December; 20(12):1844-9.

---

The invention claimed is:

1. A combination comprising:
   an amount of an inhibitor of a DNA base excision repair enzyme useful in the combination in the treatment of cancer, and
   an amount of an inhibitor of functional expression of NEAT1 acting at the RNA level,
   wherein the inhibitor is selected from the group consisting of a gapmer, an shRNA or an siRNA that hybridizes to NEAT1 RNA in a cell.

2. The combination of claim 1, wherein the inhibitor of a DNA base excision repair enzyme is a PARP inhibitor.

3. A method of treating a solid tumor in a subject in need thereof, the method comprising:
   inhibiting functional expression of NEAT1 in the subject by administering to the subject the combination of claim 1.

4. A method of identifying a solid tumor suitable for treatment with an inhibitor of functional expression of NEAT1, wherein the inhibitor is the combination of claim 1, the method comprising:
   determining whether expression of NEAT1 is increased in the tumor or in a sample of tumor cells therefrom, relative to NEAT1 expression in non-tumor tissue, thus establishing whether the tumor is suitable for treatment, wherein increased expression is indicative of suitability for treatment.

5. The method according to claim 4, wherein the solid tumor is a carcinoma.

6. The method according to claim 4, wherein expression of the long isoform of NEAT1 is determined.

7. The method according to claim 4, wherein NEAT1 expression is evaluated by determining the presence of paraspeckles.

8. The method according to claim 5, wherein expression of the long isoform of NEAT1 is determined.

9. The method according to claim 5, wherein NEAT1 expression is evaluated by determining the presence of paraspeckles.

10. The method according to claim 3, wherein the solid tumor is a carcinoma.

11. The method according to claim 3, wherein the solid tumor is selected from the group consisting of breast cancer, skin cancer, osteosarcoma, colorectal cancer, and neuroblastoma.

12. The method according to claim 3, wherein administration of the combination-therefor selectively induces apoptosis in cancer cells in the subject.

13. A method of treating a subject diagnosed as having a solid tumor selected from the group consisting of breast cancer, skin cancer, osteosarcoma, colorectal cancer, and neuroblastoma, the method comprising:
   inhibiting expression of NEAT1 in the subject by administering the combination of claim 1 in such a manner as to treat the subject for the solid tumor.

* * * * *

SEQUENCE LISTING

```
<160> NUMBER OF SEQ ID NOS: 4

<210> SEQ ID NO 1
<211> LENGTH: 53
<212> TYPE: DNA
<213> ORGANISM: Artificial Sequence
<220> FEATURE:
<223> OTHER INFORMATION: p53 shRNA sequence

<400> SEQUENCE: 1
gactccagtg gtaatctact tcaagagagt agattaccac tggagtcttt ttt          53

<210> SEQ ID NO 2
<211> LENGTH: 14
<212> TYPE: DNA
<213> ORGANISM: Artificial Sequence
<220> FEATURE:
<223> OTHER INFORMATION: NEAT1-Gapmer4

<400> SEQUENCE: 2
gacgtaacag aatt                                                     14

<210> SEQ ID NO 3
<211> LENGTH: 16
<212> TYPE: DNA
<213> ORGANISM: Artificial Sequence
<220> FEATURE:
<223> OTHER INFORMATION: NEAT1-Gapmer5
```

```
<400> SEQUENCE: 3 taagcactt  ggaaag                                                     16

<210> SEQ ID NO 4
<211> LENGTH: 15
<212> TYPE: DNA
<213> ORGANISM: Artificial Sequence
<220> FEATURE:
<223> OTHER INFORMATION: NEAT1-Gapmer6

<400> SEQUENCE: 4
ctcacacgtc catct                                                      15
```